United States Patent
Lin

(10) Patent No.: US 12,357,606 B2
(45) Date of Patent: Jul. 15, 2025

(54) COMPOSITIONS AND METHODS FOR TREATING DEFECTS IN AVASCULAR CARTILAGINOUS TISSUE BY DIRECTLY ADMINISTERING ONE OR MORE METABOLITES OF SIMVASTATIN

(71) Applicant: University of Cincinnati, Cincinnati, OH (US)

(72) Inventor: Chia-Ying James Lin, Mason, OH (US)

(73) Assignee: University of Cincinnati, Cincinnati, OH (US)

( * ) Notice: Subject to any disclaimer, the term of this patent is extended or adjusted under 35 U.S.C. 154(b) by 66 days.

(21) Appl. No.: 18/224,898

(22) Filed: Jul. 21, 2023

(65) Prior Publication Data

US 2023/0381136 A1 Nov. 30, 2023

Related U.S. Application Data

(62) Division of application No. 16/613,510, filed as application No. PCT/US2018/032635 on May 15, 2018, now Pat. No. 11,744,821.

(60) Provisional application No. 62/506,104, filed on May 15, 2017.

(51) Int. Cl.
*A61K 31/366* (2006.01)
*A61K 9/00* (2006.01)
*A61P 19/04* (2006.01)

(52) U.S. Cl.
CPC .......... *A61K 31/366* (2013.01); *A61K 9/0019* (2013.01); *A61P 19/04* (2018.01)

(58) Field of Classification Search
CPC .. A61K 31/222; A61K 31/366; A61K 9/0019; A61K 9/06; A61K 47/32; A61P 19/00; A61P 19/04
See application file for complete search history.

(56) References Cited

U.S. PATENT DOCUMENTS

| | | | |
|---|---|---|---|
| 6,866,842 B1 * | 3/2005 | Chancellor | A61P 13/10 424/93.3 |
| 2010/0111829 A1 | 5/2010 | Drapeau | |
| 2011/0053113 A1 | 3/2011 | Schnabelrauch et al. | |
| 2012/0202256 A1 | 8/2012 | Yun | |

FOREIGN PATENT DOCUMENTS

| | | |
|---|---|---|
| EP | 1036563 A1 | 3/2000 |
| JP | 2011512921 A | 4/2011 |
| WO | 200053173 A1 | 9/2000 |
| WO | 2009092094 A2 | 7/2009 |
| WO | 2009106502 A2 | 9/2009 |
| WO | 2015089089 A1 | 6/2015 |

OTHER PUBLICATIONS

Ellison et. al., "Simvastatin", Analytical Profiles of Drug Substances and Excipients, vol. 22, p. 359 (abstract), publ. 1993 (Year: 1993).*
International Search Report and Written Opinion of corresponding PCT Application No. PCT/US2018/032635 mailed Jul. 30, 2018.
Khera, et al., "Generation of statin drug metabolites through electrochemical and encymatic oxidations," Anal Bioanal Chem (2013) 405: 6009-6018.
Extended European Search Report (EESR) for corresponding EP Application No. 18801700.8 mailed Jan. 20, 2021.
Gopinathan, Current Concepts in the Articular Cartilage Repair and Regeneration; Journal of Orthopaedics, 14 (2017), A1-A3.
Oryan, et al., "Potential mechanisms and applications of statins of osteogenesis: Current Modalities, conflicts and future directions", Journal of Controlled Release, pp. 12-24, 2015.
Sugiyama, T. et al. "Subcutaneous administration of lactone form of simvastatin stimulates ectopic osteoinduction by rhBMP-2" Oral Diseases, 2007, pp. 228-233, vol. 13.
Yoshinari, M. et al. "Controlled Release of Simvastatin Acid Using Cyclodextrin Inclusion System" Dental Materials Journal, 2007, pp. 451-456, vol. 26(3).
Simoes et. al., Macromolecular Bioscience, vol. 13, p. 723-734, publ. 2013 (Year: 2013).
Montazerolghaem et. al., J. Biomedical Materials Res. A, vol. 102A, pp. 340-347, publ. online May 14, 2013 (Year: 2013).
JP Office Action Notification of Reasons for Rejection dated May 6, 2022 pertaining to JP application No. 2019-563365 1led Nov. 15, 2019, pp. 1-5.
CN First Office Action dated Apr. 29, 2022 pertaining to CN application No. 201880037675.X filed Dec. 6, 2019, pp. ~-13.

* cited by examiner

*Primary Examiner* — Sarah Pihonak
(74) *Attorney, Agent, or Firm* — DINSMORE & SHOHL LLP

(57) ABSTRACT

Controlled release hydrogel formulations of one or more simvastatin metabolites 3'-hydroxy simvastatin (hSV), 6'-exomethylene simvastatin (eSV), 3',5'-dihydrodiol simvastatin, 3',5'-dihydrodiol simvastatin (dSV), simvastatin-beta-hydroxy acid (SVA), and methods for the treatment of patients suffering from injured or degenerating substantially avascular cartilaginous tissue.

17 Claims, 11 Drawing Sheets

COMPOSITIONS AND METHODS FOR TREATING DEFECTS IN AVASCULAR CARTILAGINOUS TISSUE BY DIRECTLY ADMINISTERING ONE OR MORE METABOLITES OF SIMVASTATIN

CROSS-REFERENCE TO RELATED APPLICATIONS

This application is a divisional of U.S. application Ser. No. 16/613,510, filed Nov. 14, 2019, which is a national stage entry under 35 U.S.C. § 371 of International Application No. PCT/US2018/032635, filed May 15, 2018, and claims priority to U.S. Provisional Application Ser. No. 62/506,104 filed May 15, 2017, the entire disclosures of which are incorporated herein by reference.

TECHNICAL FIELD

Embodiments of the invention relate generally to therapeutic pharmacology and specifically to methods and compositions effective for treating subjects suffering from diseases and conditions characterized by damaged or otherwise defective cartilaginous tissue, namely, avascular cartilaginous tissue, by direct administration of one or more metabolites of simvastatin to the avascular tissue.

BACKGROUND

Simvastatin (SV) is currently a widely prescribed drug for the treatment of cardiovascular disease/hypercholestemia, and its derivatives are used in many other 25 applications including, most recently, for promoting chondrogenesis in intervertebral disk cells and improving intervertebral disk disease.

Based on examination of a library of more than 30,000 natural compounds, Mundy and co-workers discovered that the 3-hydroxy-3-methylglutaryl coenzyme A (HMG-CoA) reductase inhibitor-statins, including simvastatin (SV), are the only kind of molecule that specifically increases BMP-2 mRNA in murine and human bone cells in vitro, and induces subsequent bone formation in vivo. Statins are commonly-prescribed cholesterol-lowering drugs that inhibit the cholesterol biosynthesis pathway. Ever since the discovery of this "side-effect" on bone anabolism, bone-protective effects of statins and the underlying mechanism have become subjects of intense studies, including as a regimen for osteoporosis. Further studies also demonstrated that SV increases BMP-2 expression in various cell types such as non-transformed osteoblastic cells, bone marrow stromal cells, human vascular smooth muscle cells, and rat chondrocytes (see, e.g. Zhang, H. et al. (2008) *Spine*, 33(16), Zhang, H. et al. (2009) *Arthritis Res Ther Arthritis Research & Therapy*, 11(6), and Than, K. D. et al. (2014) *The Spine Journal*, 14(6), 1017-1028, the entire disclosures of which are incorporated herein by reference).

Degenerative disc disease (DDD) is considered the leading contributor to low back pain, a common medical problem that also engenders a significant socioeconomic burden. The current clinical standards for the treatment of DDD, however, are often associated with complications, particularly when surgical interventions are involved. Biological repair or regeneration of the degenerative intervertebral disc (IVD) has been advocated with recent advances in recombinant therapeutic proteins, including recombinant human bone morphogenetic protein-2 (BMP-2). However, the required doses of these recombinant human growth factors are often supra-physiological, raising concerns about potential for toxicity and other undesirable complications.

As alternatives to the current treatment regimen, over the past decade, tissue engineering and regenerative approaches have become a topic of intense research efforts. In particular, growth factors such as bone morphogenetic protein (BMP) family have shown great promise in stimulating matrix regeneration within damaged disc tissue. While initial results are encouraging, clinical use of recombinant growth factors raises a host of concerns including: undesired growth of blood vessel within otherwise avascular disc tissue, supra-physiologic concentration required for therapeutic effectiveness, which increases the risk of side effects, and the high costs associated with production of clinical grade recombinant proteins. Therefore, regenerative medicines that are devoid of such issues are more desired.

For more than a decade, the present investigators have extensively studied the effects of SV, and have reported that SV stimulation promotes several phenotypic expressions of mammalian nucleus pulposus (NP) cells, including aggrecan, type II collagen, as well as sulfated glycosaminoglyca, which in turn helps retard the progression of degeneration and facilitate the repair of the degenerated IVD. It was discovered that SV is efficacious to promote chondrogenesis by upregulating endogenous BMP-2 expression in the treated NP cells, which in turn facilitates repair of the affected IVD in vivo. Additional benefits of proposed SV treatment for DDD also included that the intradiscal injection procedure does not require an open surgery, which minimizes postoperative pain and recovery time as well as the risk of excessive disc perturbation that eventually leads to deformative degeneration. The procedure is common and can be performed by many other clinical specialists in addition to spine surgeons, making such approach more affordable, practical, and adoptable in the current healthcare system. Thus, SV is considered a promising alternative to protein-based regenerative medicine for the treatment of DDD.

Based on the similarities between intervertebral disk and meniscal composition, direct administration of SV has also been considered for utilization in the treatment of meniscal tissue defects to improve healing by stimulating chondrogenesis in a similar manner as in the intervertebral disk model. A meniscal tear is one of the most common injuries of the knee, resulting in substantial loss of productivity and reduced quality of life for a large percentage of the population, even among younger people. Physicians report that approximately one third of people over 50 have at least one torn menisci, making this population more vulnerable to instability/falls and chronic pain as they approach an advanced age.

The present investigators previously utilized a well-known meniscal injury model, wherein a biopsy punch or k-wire is used to create a circular, full thickness lesion in the meniscus, and using sustained drug delivery of SV in conjunction with an FDA approved biodegradable hydrogel, demonstrated new tissue growth within four weeks of injection (see Zhang & Lin, (2008) *Spine*, 33(16), and Zhang et al. (2016) *The American Journal of Sports Medicine*. doi: 10.1177, the entire disclosures of which are incorporated herein).

It is well known that systemically delivered SV undergoes extensive first-pass metabolism in the liver. As a consequence, the drug becomes rapidly hydrolyzed to several oxidative products (FIG. 5), including 3'-hydroxy SV (hSV), 6'-exomethylene SV (eSV), 3',5'-dihydrodiol SV (dSV), and SV beta-hydroxy acid (SVA). Some of the hydroxy acid forms of these metabolites, including SVA, were also discovered to be HMG-CoA reductase inhibitors, and SVA was thereafter found to be a competitor to SV. Therefore, one may presume that at least some of the therapeutic effects attributed to systemically administered SV actually implicates one or more of the SV metabolites.

Critically, however, direct injection of SV into the IVD or joint space would not be expected to result in a presence of SV metabolites in the IVD or joint space, both of which are avascular (having an absence of vessels which conduct or circulate blood or lymph). Direct injection bypasses liver metabolism, and thus it may be concluded that the observed regenerative effects of SV in avascular tissues does not implicate SV metabolites and are due to the physio-pharmacology of the SV active itself.

Therefore, prior to the investigations reported herein by the present inventors, no studies have been performed to determine whether any of the metabolites of SV are similarly effective with respect to increasing BMP-2 expression in avascular tissues, especially for the metabolites known to be competitive HMG-CoA reductase inhibitors—eSV and SVA. Further, no studies have been performed to validate if SV metabolites that are non-HMG-CoA reductase inhibitors, i.e. hSV and dSV, can nonetheless regulate BMP-2 expression or modulate other cellular/molecular activities being observed. In particular with direct injection into joints and discs, potential benefits such as reducing the volume of the injection, formulation advantages, and increased potency with decreased side effects, all render further investigation of SV metabolites a compelling approach to the discovery of effective, relatively noninvasive methods for regenerating defective avascular tissue.

SUMMARY

The present investigators surprisingly determined that the SV metabolite SVA inhibits mevalonate conversion more efficiently than SV, and is 5-6 times more anabolic than SV alone in regeneration of avascular tissue upon direct administration. Further, it was discovered that SVA contributes to the anti-catabolism that synergizes to promote chondrogenesis as observed with SV. Interestingly, it was also found that administration of SV metabolites that are non-HMG-CoA reductase inhibitors, including both dSV and hSV, promoted a degree of regeneration, suggesting that an as-yet non-elucidated mechanism exists with respect to the efficacy of the metabolites. Thus, direct administration of a composition of one or more SV metabolites provides a greater regenerative benefit to the patient suffering from either DDD or meniscal injury than administration of SV alone.

Accordingly, one embodiment provides methods of repairing or retarding damage to degenerating or injured substantially avascular cartilaginous tissue. The methods comprise administering to a subject in need thereof a composition comprising at least one oxidative metabolite of simvastatin (SV) directly to the site of the avascular tissue. In other embodiments, the methods comprise administering to a subject in need thereof at least one active that increases bone morphogenic protein (BMP) expression without inhibiting HMG-CoA reductase directly to the site of the injured a vascular tissue. In specific embodiments the at least one active is selected from hSV, dSV and combinations thereof.

Another embodiment provides a controlled release composition formulated for injectable administration, said compositions comprising at least one oxidative metabolite of simvastatin (SV).

Other embodiments are directed to methods for treating patients suffering from an injury to an avascular cartilaginous tissue including but not limited to DDD and meniscal injury.

These and other embodiments will be more fully described and clarified by reference to the Figures and Detailed Description below.

BRIEF DESCRIPTION OF THE FIGURES

Figures are set forth to illustrate particular embodiments and aspects of the invention and should not be construed as limiting the full scope as defined by the appended claims.

FIG. 7A 2X Hematoxylin & Eosin histological staining (H & E) 8 weeks post injury of injury-only control showing absence of repair tissue; FIG. 7B 2X H & E at 8 weeks post injury with treatment showing presence of repair tissue.

FIG. 8A 40X H & E at 8 weeks post injury with treatment showing repair tissue; FIG. 8B 40X BMP-II immunohistochemistry at 8 weeks post injury with treatment showing repair tissue.

FIG. 9A 40X (right medial meniscus) Safranon-O staining 8 weeks post injury with treatment showing repair tissue at repair site.

FIG. 10A 40X (right medial meniscus) COL-I immunohistochemistry 8 weeks post injury with treatment showing repair tissue at repair site.

FIG. 11A 40X (right medial meniscus) COL-II immunohistochemistry 8 weeks post injury with treatment showing repair tissue at repair site.

Figure 1A:
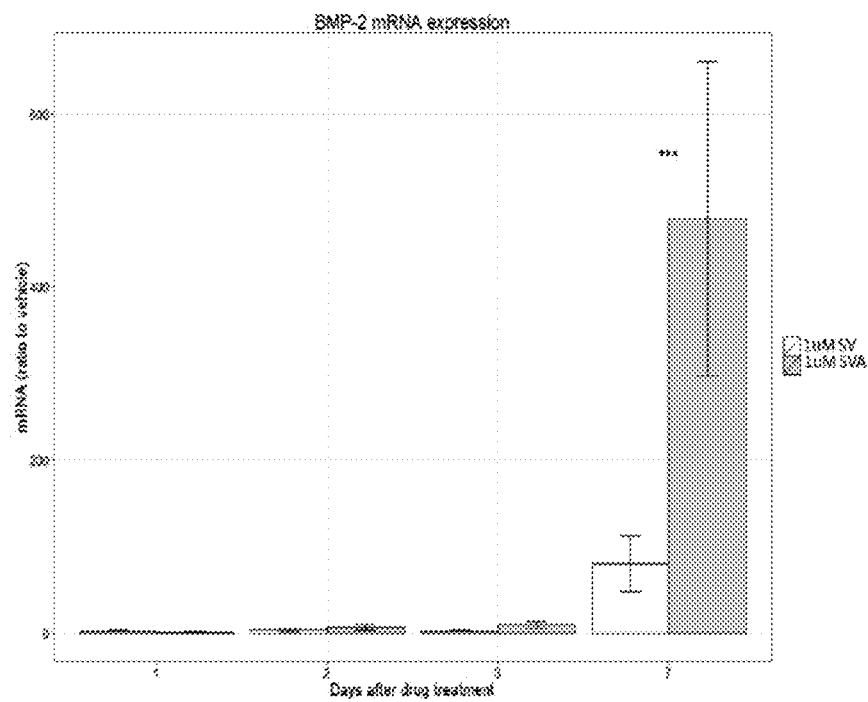
FIG. 1A shows the effect of simvastatin (SV) and simvastatin hydroxy acid (SVA) at 1 µM, and FIG. 1B 3 µM on BMP-2 mRNA expression in rat NP cells. Data are normalized with GAPDH and are expressed as ratio to vehicle (DMSO).

11A showing positive staining of organized cells for COL-II located in the inner ⅓ of meniscal tissue.

DETAILED DESCRIPTION

Low back pain (LBP) is one of the most common medical problems in the U.S., plaguing about 80% of the U.S. population at some point in their lives. It is also one of the most prevalent reasons for missed work, and chronic LBP fuels narcotics dependency; thus imposing an enormous socioeconomic burden as well as public health problem. Among cases of LBP that are either specific (e.g. spinal tumor or infection) or non-specific (without apparent causes), degenerative disc disease (DDD) has been considered as the primary contributor to LBP. The current clinical standards to treat DDD are often associated with complications, particularly when surgical interventions are involved. The ability to biologically repair or regenerate the aberrant disc in situ with therapeutic compounds is therefore an attractive choice for future treatment options. Such a strategy is appealing not only because it provides the least invasive intervention, but also because it potentially facilitates reconstitution of the injured disc.

The currently available reconstitution regimen involves using recombinant growth factors, which are not only prohibitively high in cost to manufacture, but also pose concerns about toxicity and other undesirable complications associated with the supra-physiological doses required. Thus, unfortunately, the current standard of care for DDD focuses on pain control, stabilization of the spine, and deceleration of disease progress rather than disc repair.

The present inventors previously revealed that simvastatin (SV), a 3-hydroxy-3-methylglutaryl-CoA (HMG-CoA) reductase inhibitor commonly prescribed as a cholesterol-lowering drug, promotes phenotypic expression of mammalian nucleus pulposus (NP) cells when treated with drug in vitro. In vivo, when affected intervertebral disc (IVD) in a rat model of DDD was injected with a controlled release formulation of SV, the compound retarded the progression of degeneration and most notably also facilitated the repair of the degenerated IVD (the anabolism). In addition, the known pleiotropic effect of simvastatin in anti-inflammation was also observed, in which the expression of enzymes that degrade extracellular matrix was suppressed (the anti-catabolism). These matrix metalloproteinases (MMPs) are typically stimulated by pro-inflammatory cytokines in a pathological disc. The results provide initial evidence that SV is a better alternative to recombinant proteins for treating DDD. Nonetheless, hydrophobicity of the SV pro-drug also significantly limits its local delivery with currently available/approved hydrogel vehicles.

Provacatively, in a most recent study undertaken by the present inventors, it was observed that an active hydrolytic metabolite of SV, simvastatin beta-hydroxy acid (SVA), was actually more effective in upregulating endogenous bone morphogenetic protein-2 (BMP-2), the mediator of the consequent disc repair seen with the pro-drug SV, suggesting that at least one of the SV metabolites may dictate the efficacy of SV observed in treatment of IVD.

The NP cells are normally referred as "chondrocyte-like" cells because these cells are initially notochordal but are gradually replaced during childhood by rounded cells resembling the chondrocytes of articular cartilage. The NP cells maintain the chondrogenic phenotype for the constitution of the IVD tissue matrix and exposure of NP cells to BMP-2 promotes the expression of chondrogenic phenotype. Moreover, a recent finding also indicated that endogenously produced BMPs, including BMP-2, interfere with the effects of pro-inflammatory cytokines. Both phenomena coincide with the results described earlier. This experiment is designed to show that stimulated BMP-2 expression in avascular tissue is enhanced by administration of the active metabolite SVA, which is also a potent competitor in inhibiting HMG-CoA reductase, and by composition comprising SVA and at least one addition SV metabolite, as well as by compositions comprising SV and at least one active SV metabolite, including metabolites that are not HMG-CoA reductase inhibitors.

Statins are potent inhibitors of cholesterol biosynthesis. However, ongoing continuous studies also indicate that some of the cholesterol-independent or "pleiotropic" effects of statin are more beneficial than what might be expected from changes in lipid levels alone. Statins, including SV, affect the enzymatic activities of protein prenylation that is critical for the functions of down-stream small G-proteins. These G-proteins are the modulators of many physiological responses and intracellular signaling pathways including polarity, gene transcription and intracellular vesicular transport. Thus, there is particular interest in the effects of SV metabolites on the Rho family, and its sub-family Rac, G-proteins. SV exerts anti-inflammatory actions by inactivating Rho, which is related to what was observed in the suppression of MMPs. Rac, on the other hand, when inhibited by SV, reduces oxidative stress. Recent studies have reported that induced oxidative stress in the NP cells is associated with disc degeneration. Thus it is important to elucidate the role of SV metabolites in the down-regulation of the two G-proteins observed with the SV pro-drug.

Figure 5:
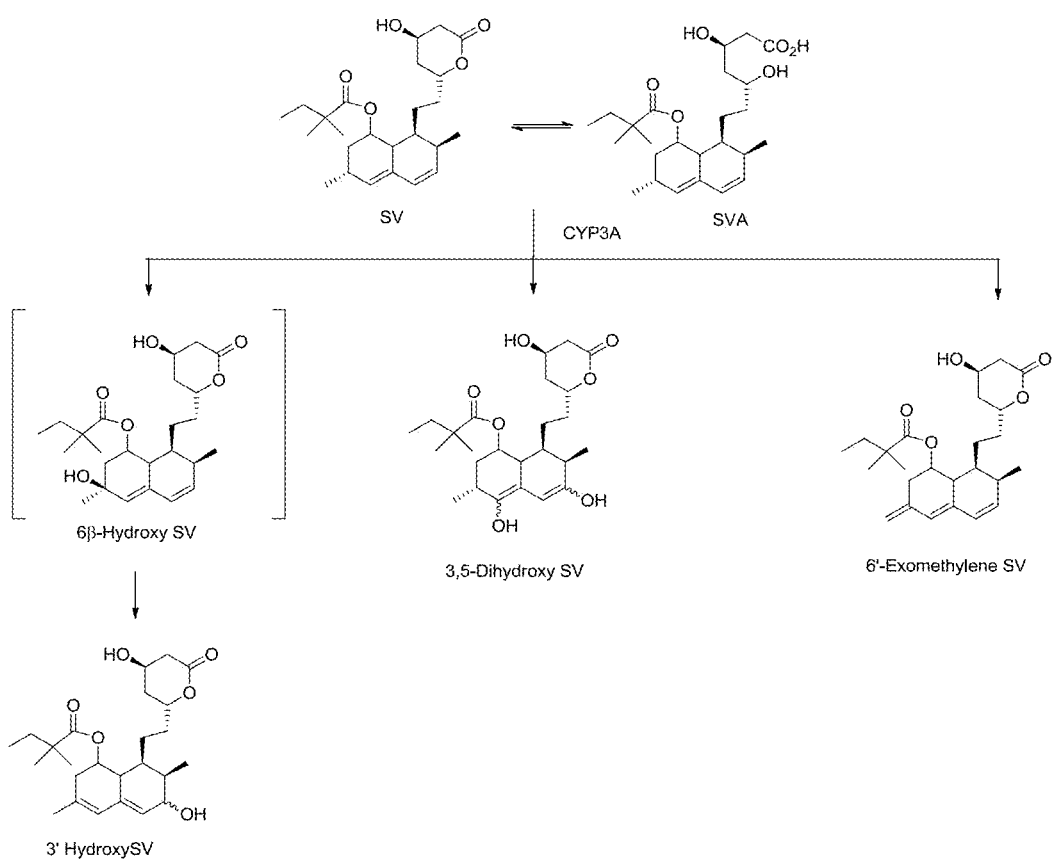
FIG. 5 sets forth structures and pathways of simvastatin and its metabolites.
Figure 6A:
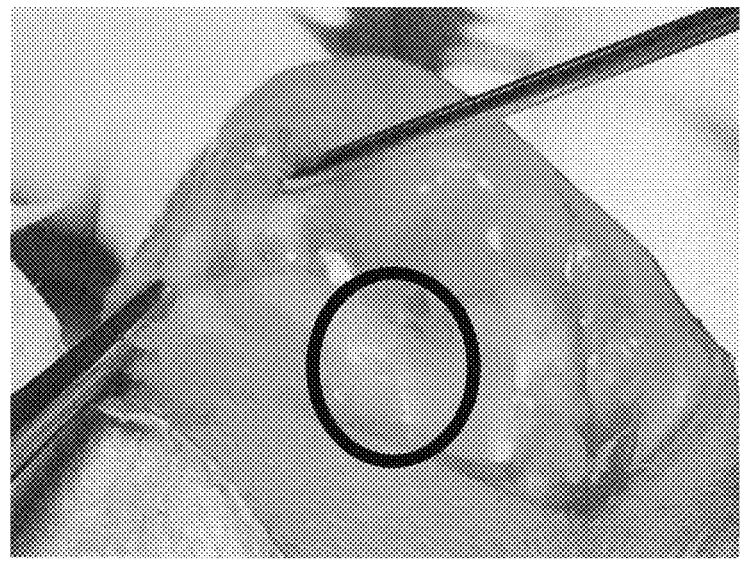
FIG. 6A photograph showing completed 1.4 mm defect of right medial meniscus.
Figure 6B:
FIG. 6B photograph showing injection of hydrogel composition to left medial meniscus.
Figure 7A:
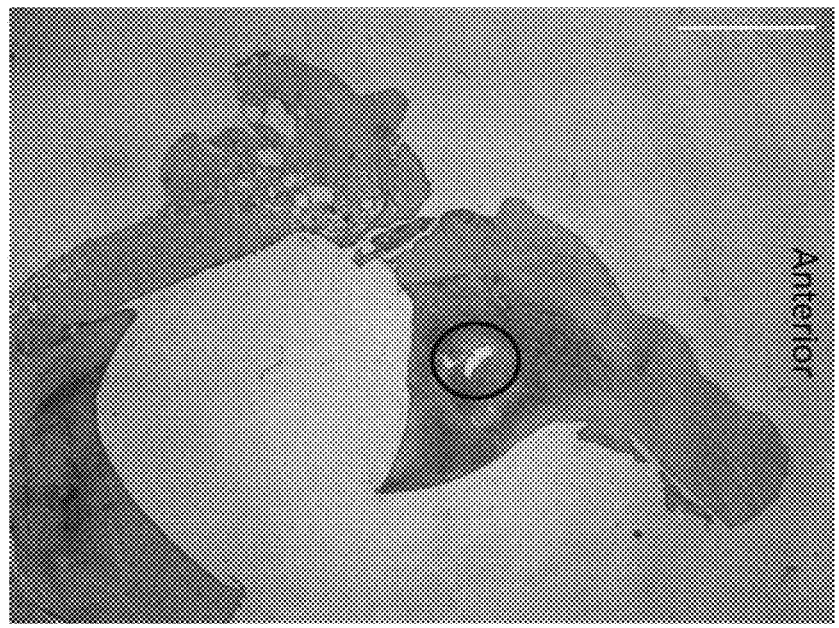
Figure 7B:
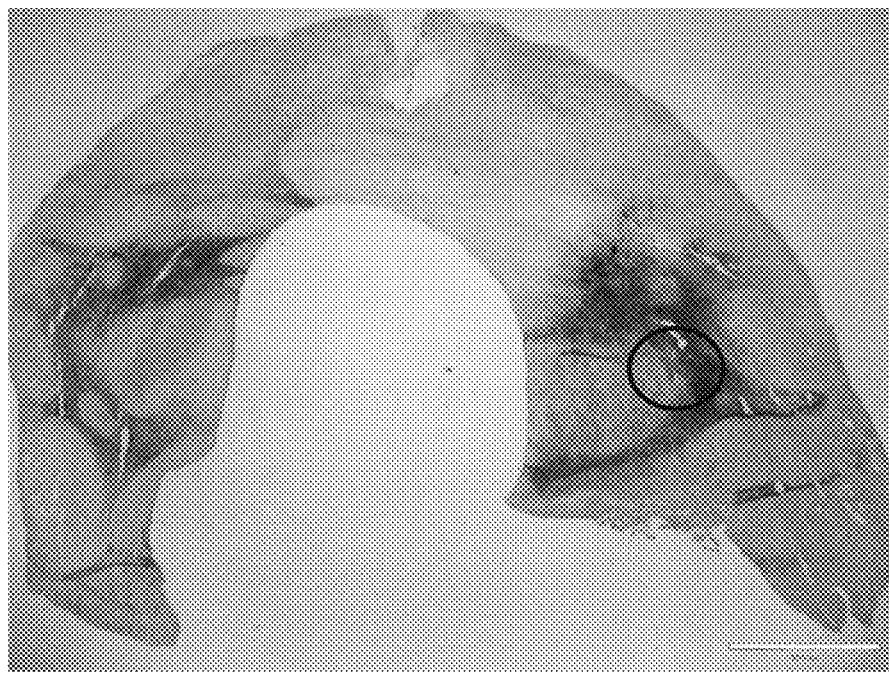

In systemic delivery, SV undergoes hepatic metabolism, generating various metabolites including several hydroxy acids such as SVA (see FIG. 5). These acidic metabolites can compete the pro-drug SV in the rate-limiting enzymatic activities, and potentially be influential for certain biological activities. However, with respect to delivery to avascular tissue, neither systemic administration nor administration directly of SV would be expected to provide active metabolites.

As described earlier, the discovery of the pleiotropic effect of statins on BMP-2 upregulation has engendered intense investigation, particularly for their implications in bone anabolism and bone protection. Extended studies have been also conducted to elucidate the underlying mechanism for the upregulation, and the results indicate that statins increase the expression of BMP-2 through the Ras/PI3K/Akt/MAPK (mitogen-activated protein kinase)/BMP-2 pathway (Ghosh-Choudhury N et al. J Biol Chem. 2007; 282(7)). Chen et al. (Chen P. Y. et al. Nutr Res. 2010; 30(3):191-9) confirmed these results and further reported that the PI3K/Akt pathway for statin-induced osteogenesis is dependent on the activation of a small GTPase, Ras, which is promoted by localizing the protein on the intracellular membrane. In addition to bone, BMPs have also been implicated as potential therapeutic agents for IVD degeneration with studies focusing on the use of BMPs 2, 4, 7 and 14. All of these growth factors act on the same receptors which require the presence of BMPRII to function. However, only one study has investigated the expression of this receptor in human IVD tissue. Wang H. et al. (J Mol Med-Jmm. 2004; 82(2):126-34) used reverse transcriptase PCR to demonstrate the expression of the BMP receptors in six human scoliotic IVD discs and showed that mRNA for the three receptors were expressed.

In Example 1, BMPRII is localized to the cells of the NP and inner annulus fibrosus (AF) of 30 human intervertebral discs. Little immunopositivity was seen in cells from the outer AF. Cells in the NP showed higher proportions of immunopositivity than in the inner AF. This suggests that the BMPs applied to the human IVD would show greatest effects within the NP and inner AF. These results differ from those observed in mice, where receptor expression has only been observed in the cartilaginous end plate and AF. Interestingly no change in levels of expression were observed with the degree of degeneration.

Figure 1B:
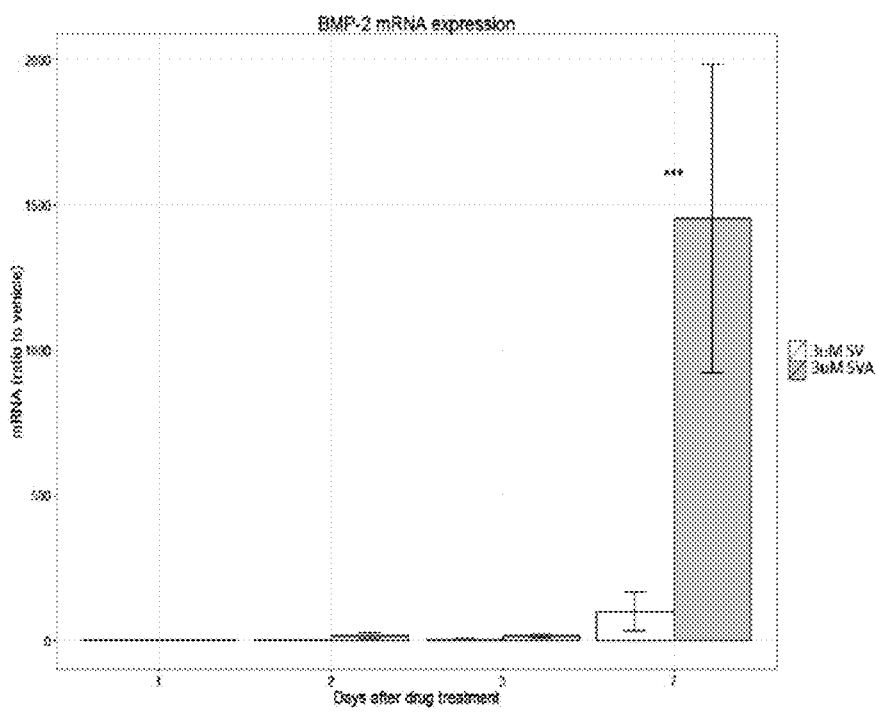

Findings from the investigation on SV stimulating endogenous BMP-2 expression in the treated NP cells, which in turn increases chondrogenic phenotype expression (aggrecan and type II collagen mRNA expression as well as sGAG content), were consistent with the above observations, validating that the small molecule is as efficacious in promoting chondrogenesis as to osteogenesis. Surprisingly, however, upregulation of BMP-2 was stimulated to a much greater extent when these cells were treated with SVA, an active hydrolytic metabolite of SV. SV has been prescribed widely for the treatment of hypercholesterolaemia and hypertriglyceridaemia. In humans, it undergoes rapid metabolism to form four major oxidative, NADPH-dependent metabolites, 3'-hydroxy SV (hSV), 6'-exomethylene SV (eSV), 3',5'-dihydrodiol SV (dSV), and SVA (FIG. 5). Among them, SVA is the most potent competitor of SV in HMG-CoA reductase inhibition. This raised the question as to whether SVA is dominant in the entire scheme of BMP-2 upregulation. To test whether the levels of induced-BMP-2 by both SV and SVA, respectively, would be any different, the present investigators used the in vitro model system developed in the prior study to conduct the test. Rat NP cells harvested from tail discs were cultured initially in monolayer and then in alginate beads (Zhang H. et al. *Spine*, 2008; 33(16), the entire disclosure of which is incorporated herein by reference). Cells were treated with DMSO (vehicle), SV or SVA at 1 or 3 µM. Cells were then collected at predetermined time points and with RNA extracted. Gene expression was analyzed by RT-qPCR. The result showed that, at 1 µM, mRNA expression of BMP-2 was the same or doubled in cells treated with SVA compared to that in cells treated with SV from Day 1 to 3. However, the difference was then dramatically increased at Day 7. The BMP-2 level induced in the SVA group was 5-6 times higher than that in the SV one (FIG. 1A). The difference was further augmented when the treating concentrations were increased to 3 µM (FIG. 1B).

The result indicated superior effectiveness of SVA over SV on BMP-2 upregulation. The event of BMP-2 upregulation is a consequence of HMG-CoA reductase inhibition, which can be achieved by SV, SVA, and eSV as they are all inhibitors. Further surprising, some regenerative potential is established by administration of the non-HMG-CoA reductase inhibitors hSV and dSV, although the pathway is unclear.

Figure 2:
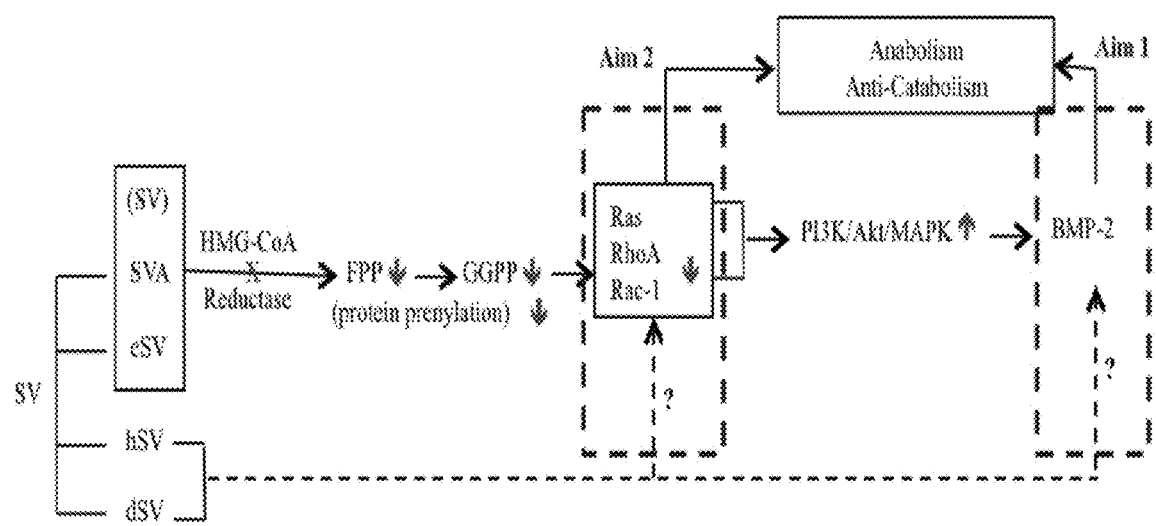
FIG. 2 sets forth a schematic illustration of the effects of SV metabolites on the observed IVD repair with SV.

It is known that SV can block the synthesis of either isoprenoid intermediates, farnesyl pyrophosphate (FPP) or geranylgeranyl pyrophosphate (GGPP), which in turn inhibit the function of down-stream small G-proteins such as Ras, Rho, Rab family. The question of a mechanistic pathway (do they affect protein prenylation or the G-proteins directly) for the effects of the non-HMG-CoA reductase inhibitors hSV and dSV remains open. As Ras and Rho regulate the expression of BMP-2 through the Ras/PI3K/Akt/MAPK/BMP-2 pathway, and both Rho and Rac can be related to the anabolic and anti-catabolic effects observed, dissecting the mechanisms of how the metabolites contribute to the efficacies obtained with SV provides additional therapeutic strategies. A scheme illustrating this is set forth in FIG. 2.

Figure 3A:
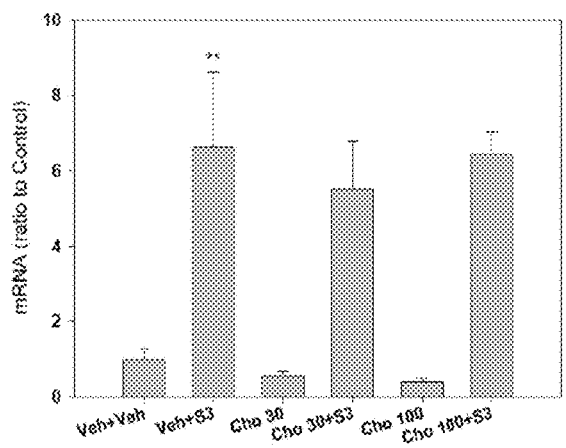
FIG. 3A demonstrates that when treated with 3 µM (an effective dose in vitro) SV, the upregulated BMP-2 mRNA expression in the rat NP cells was independent of the presence of cholesterol.
Figure 3B:
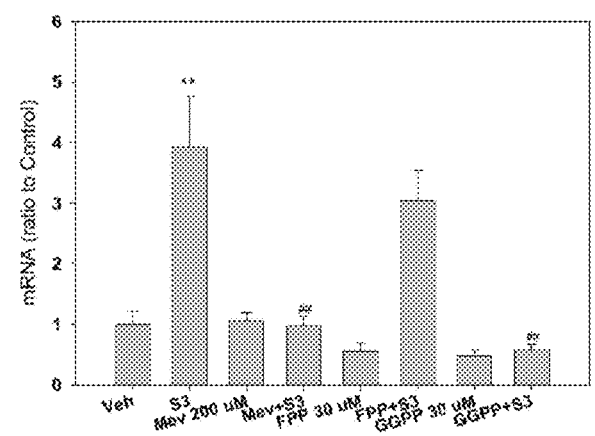
FIG. 3B shows that the stimulation was excluded from the inhibition of FPP, but highly affected by the inhibition of the downstream substrate GGPP along the MVA pathway.
Figure 3C:
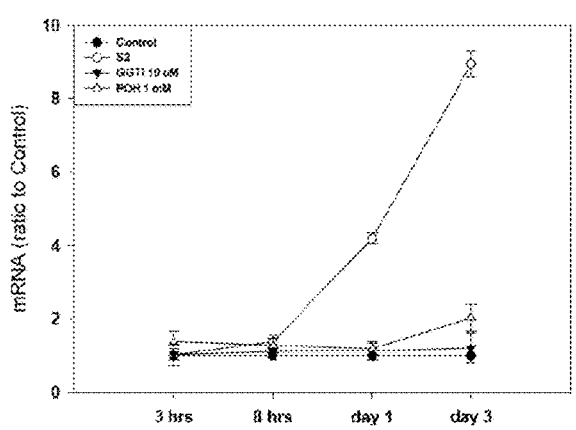
FIG. 3C shows that inhibition of individual GGTase achieved the stimulation of BMP-2, but the level was not comparable to that stimulated by simvastatin directly.
Figure 3D:
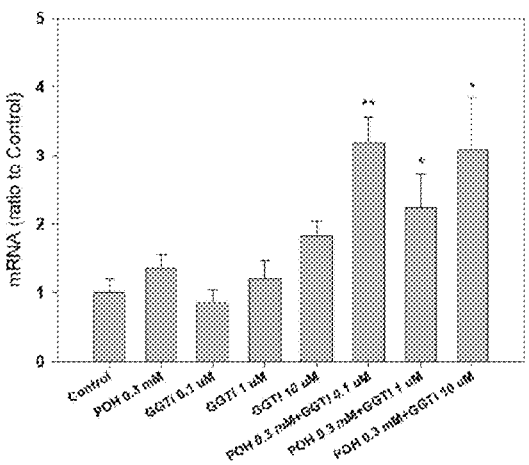
FIG. 3D shows that when both inhibitions appeared concurrently, the stimulation significantly increased compared to each inhibition alone, although the level was still below the expression promoted by simvastatin.

The classic mechanism understood for cholesterol lowering by statins is that statins act by competitively inhibiting HMG-CoA reductase, the first committed enzyme of the mevalonate (MVA) pathway. This competition reduces the rate by which HMG-CoA reductase is able to produce MVA, the next molecule in the cascade for the synthesis of prenylation enzyme substrates FPP and GGPP that eventually help produce cholesterol. As indicated previous studies by the inventors (Zhang H. N., Lin C. Y. *Spine*. 2008; 33(16), fully incorporated herein by reference), when SV was present, BMP-2 mRNA expression of NP cells always responded in a time and dose-dependent manner. Furthermore, the stimulation in the NP treated with 3 µM SV was independent of the presence of cholesterol (FIG. 3A), as well as FPP (FIG. 3B). Instead, the stimulation was actually involved in the MVA pathway, as indicated by the observation that the stimulation was completely reversed when cells were pre-treated with MVA. Interestingly, the reversion was also achieved when the downstream substrate GGPP was supplemented (FIG. 3B). Next, when either of the GGTase inhibitors, GGTI-286 and POH, was given to mimic the inhibition of GGPP enzymatic activation by SV, both of them were able to increase BMP-2 mRNA expression, but the level was much lower than that found with SV, respectively (FIG. 3C). When IVD cells were co-treated with GGTI 286 and POH together, the BMP-2 upregulation was significantly higher than with each treatment alone (FIG. 3D). However, the BMP-2 upregulation by the co-treatment yet still did not reach a comparable level to that with the SV treatment, suggesting a mechanism separate from the inhibition of HMG-CoA reductase may synergistically promote the BMP-2 expression. Without being bound by mechanism, the present inventors have discovered that SV metabolites that are not HMG-CoA reductase inhibitors, i.e. hSV and dSV, also affect BMP-2 upregulation.

One embodiment is directed to methods for repairing or retarding damage to injured substantially avascular cartilaginous tissue, the method comprising administering to a subject in need thereof a composition comprising at least one oxidative metabolite of simvastatin (SV) directly to the site of the avascular tissue. According to more specific embodiments, the step of administering comprises administering a controlled release formulation of the at least one oxidative metabolite of simvastatin (SV), wherein said composition is released in said avascular cartilaginous tissue at a rate and an amount effective to permit repairing or retarding damage. The at least one oxidative metabolite of SV is selected from the group consisting of 3'-hydroxy simvastatin (hSV), 6'-exomethylene simvastatin (eSV), 3',5'-dihydrodiol simvastatin, 3', 5'-dihydrodiol simvastatin (dSV), simvastatin-beta-hydroxy acid (SVA), and combinations thereof. According to very specific embodiments, the at least one oxidative metabolite of SV comprises SVA.

It is contemplated that in some embodiments SV may be administered in conjunction with the at least one metabolite, wherein "in conjunction" includes simultaneous administration, tandem administration, or administration within a therapeutic time frame. Where administration is simultaneous, it may be as one dosing unit or as multiple units. A therapeutic time frame may be any time frame during which the patient is undergoing therapy for injured or degenerated cartilaginous tissue. A therapeutic regimen may include a single administration or multiple administrations over the therapeutic time frame. According to very specific embodiments the cartilaginous tissue comprises spinal disc cartilage/fibrocartilage, and in other specific embodiments the cartilaginous tissue is in a joint. According to an even more specific embodiment the cartilaginous tissue comprises meniscal cartilage.

According to some aspects, where the subject suffers from degenerative disc disease, administering comprises administering to directly into an intradiscal space, for example by injecting or by guided catheter. Injecting may be carried out using a fluoroscope to guide a syringe carrying a formulation, for example a controlled release composition of one or more of metabolites with our without SV. Administering the controlled release composition promotes proliferation of chondrocytes or chondrocyte-like cells in the damaged cartilage site. According to specific embodiments the subject is a mammal, and in very specific embodiments the mammal is a human.

According to specific embodiments, controlled release compositions are provided that comprise one or more hydrogels comprising the active. Exemplary hydrogels suitable for drug delivery formulations include chitosan (CT), cyclodextrin (CD), p-dioxanone (DX), ethylene glycol (EG), ethylene glycol dimethacrylate (EGDMA), hyaluronic acid (HA), hydroxyethyl methacrylate (HEMA), methylene-bis-acrylamide (MBAAm), poly(acrylic acid), Polyacrylamide, poly-caprolactone, poly(ethylene glycol), poly(ethylene imine), poly(ethylene oxide), poly(ethyl methacrylate), poly(hydroxyethyl methacrylate), poly(hydroxypropyl methacrylamide), poly(lactic acid) (PLA), poly(lactic-co-glycolic acid) (PLGA), poly(methyl methacrylate) (PMMA), poly(propylene oxide), poly(vinyl alcohol) (PVA), poly(vinyl acetate), poly(vinyl amine), and combinations thereof.

According to some embodiments, the hydrogel comprises a hydrophobic polymer and a hydrophilic polymer, and in some embodiments the polymers are homopolymers or copolymers. The hydrophilic polymer may be included in a range of from about 10% to 50%, from about 20% to 40%, or from about 20% to 30%, and the hydrophobic polymer may be included in the hydrogel is in a range from 40% to 90%, from about 60% to 80%, or from about 70%-80%. According to very specific embodiments, the hydrophilic polymer comprises. In other very specific embodiments the hydrophobic polymer comprises CT. Even more specifically, the HA comprises HA-Na polyanion and the CT comprises $CT-NH_3^+$ polycation, and the mass ratio of CT to HA is about 60:40. "About" in this paragraph means +/−2%. An amount of the at least one metabolite (with or without SV) is dispersed within the hydrogel matrix. The metabolite is selected from the group consisting of 3'-hydroxy simvastatin (hSV), 6'-exomethylene simvastatin (eSV), 3',5'-dihydrodiol simvastatin, 3',5'-dihydrodiol simvastatin (dSV), simvastatin-beta-hydroxy acid (SVA), and combinations thereof. According to specific embodiments, the active comprises SVA. According to other specific embodiments the active is selected from hSV, dSV, and combinations thereof. According to some embodiments, the amount of active dispersed in the controlled-release hydrogel comprises from 1 to 50 mg/ml, including all ranges and numerical amounts in between.

Another embodiment provides methods of repairing or retarding damage to injured substantially avascular cartilaginous tissue. The methods comprise administering to a subject in need thereof at least one active that increases bone morphogenic protein (BMP) expression without inhibiting HMG-CoA reductase directly to the site of the injured avascular tissue. According to specific embodiments the active is selected from hSV, dSV and combinations thereof.

The Examples are set forth to illustrate and support specific embodiments and should not be construed as limiting the full scope of the invention as defined by the appended claims.

Example 1

This Example demonstrates validity of a model system of degenerated human NP cells, and tests SV and its metabolites.

Figure 4:
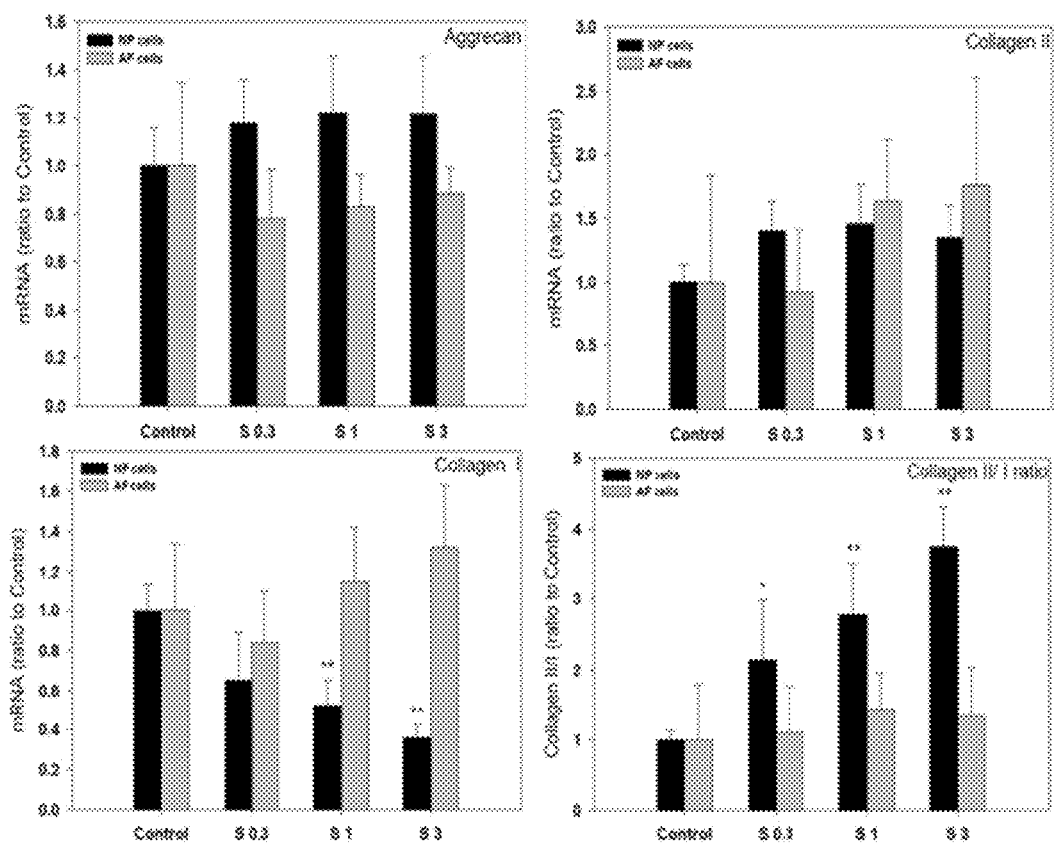
FIG. 4 illustrates the effects of simvastatin on aggrecan, collagen type II, collagen type I mRNA expression and the "differentiation index" collagen II/I ratio of the human NP and AF cells. Data are normalized with GAPDH and are expressed as ratio to Vehicle (*, P<0.05 and **, P<0.01 compared with Vehicle).

Previous publications were all based on in vitro and in vivo investigations using rodents and thus it was undertaken to establish a model system with degenerated human NP cells. Interestingly, the results show a different pattern for human cell response to the drug compared to other work with the rat and pig cells. When IVD cells harvested from human patients with DDD were exposed to SV, these cells were stimulated to maintain or even increase the chondrogenic phenotype in a dose-dependent manner. However, there were differences in the expression pattern from that in rat IVD cells (see Zhang H N, Lin C Y Spine. 2008; 33(16)). SV up-regulated BMP-2 mRNA expression in both of the human NP and annulus fibrosus (AF) cells as observed in rat cells. In addition, both the NP and AF cells expressed the BMP-2 receptor, BMPRII, indicating that both cell types are susceptible to the upregulation of BMP-2 induced by SV to mediate the determined pathways (data not shown). However, the mRNA expressions of aggrecan and type II collagen were not affected when the human NP cells were treated with SV at the same doses (0.3 to 3 µM) that were also used to treat rat cells. Alternatively, SV suppressed type I collagen mRNA expression in a dose dependent manner, and therefore significantly increased the ratio of type II to type I collagen (FIG. 4). This phenomenon was only observed in the human NP cells compared to those from other species used (rat (Zang et al. 2008), rabbit and pig, data not shown). The treatment did not change the mRNA expression of aggrecan, collagen type II and collagen type I in the human AF cells. The result of the increased ratio of Col II/Col I (also referred as "differentiation index") suggests that SV may have restrained the dedifferentiation of the human NP cells in the degenerated discs, which would have assisted the maintenance of their chondrogenic phenotype.

Based on this finding, in the present study, human NP cells are used to better facilitate the proposed strategy for the human IVD repair. However, in order to obtain a high order consistency, particularly for the experiment using CRISPR genome-editing techniques, a human NP cell line derived by Dr. Win-Ping Deng (Liu M. C. et al. Tissue Eng Part C-Me. 2014; 20(1):1-10, fully incorporated herein by reference) from Taipei Medical University and Hospital, Taipei, Taiwan, was employed.

SV Metabolites

All compounds in the study, including SVA, eSV, hSV, and dSV, were synthesized and characterized (e.g. chemical structure, solubility, particle size, impurity, and polymorph) by AAPharmaSyn, LLC, a global chemistry contract research organization founded and operated by former Pfizer chemists who have extensive knowledge and experience with statins, including the success in developing LIPITOR® (atorvastatin). The group also developed the two SV metabolites that are non-HMG-CoA reductase inhibitors, hSV and dSV for the studies.

Treatment Designs

Immortalized human NP (ihNP) cells are expanded followed by encapsulation with alginate beads to maintain their phenotype in a three-dimensional environment as previously described (Zang et al. 2008). The newly formed alginate beads are cultured in each well of a 6-well plate and placed in DMEM/F12 medium with 10% FBS media+2 mM L-glutamine+50 µg/mL vitamin C. Three days later, the medium is changed and the cells are treated with 0.3, 1, and 3 µM of SV pro-drug and each of the SV metabolites, respectively, as described earlier with both of SV and SVA. Cells are removed from the alginate beads at Days 1, 2, 3, and 7 post-treatment. Cells are rinsed with 0.15 M NaCl and then incubated in the dissolving buffer (55 mmol/L sodium citrate and 0.15 M NaCl, pH 6.0) at 37° C. for 15 min. Cells are pelleted by centrifugation and the dissolved solution is collected for the assessments. Total RNA is extracted using Trizol reagent followed by RNeasy Mini Kit and DNase digestion with the RNase-free DNase set. Concentration of total RNA is determined at 260 nm with a spectrophotometer. Reverse transcription is carried out using the SuperScript First-Strand Synthesis System. Real-time polymerase chain reaction is used to quantify gene expression levels of BMP-2 using TaqMan Real-Time PCR Kit performed using the Gene Amp 7700 Sequence Detection System. The quantity of gene expression of BMP-2 is calculated with standard samples and normalized with GAPDH internal control. In addition, a combinatory treatment with all metabolites at each of the three concentrations is also performed to investigate if the overall contributions from these compounds are synergistic or antagonistic.

Example 2

This Example tests and demonstrates the effects of SV metabolites on small GTP-binding proteins (G-proteins).

Members of the Ras and Rho GTPase family are major substrates for post-translational modification by prenylation. Both Ras and Rho are small GTP-binding proteins, which cycle between the inactive GDP-bound state and active GTP-bound state. In endothelial cells, Ras translocation from the cytoplasm to the plasma membrane is dependent on farnesylation, whereas Rho translocation is dependent on geranylgeranylation. Statins inhibit both Ras and Rho isoprenylation, leading to the accumulation of inactive Ras and Rho in the cytoplasm. Because Rho is the major target of geranylgeranylation, inhibition of Rho and its downstream target, Rho-kinase, is a likely mechanism mediating some of the pleiotropic effects of statins on the vascular wall, leukocytes, and bone. Various studies have suggested that the inactivation of Rho is involved in statin-induced BMP-2 expression, which is consistent with the preliminary finding that the inhibition of GGPP by SV was shown to dominate the BMP-2 upregulation in the treated IVD cells. Moreover, Luan et al. reported that statins inhibit secretion of MMP-1, -2, -3, and -9 from vascular smooth muscle cells and macrophages and suggested that inhibition of GGPP-mediated prenylation is the mechanism for this phenomenon, as the secretion of MMP was rescued by re-application of GGPP. On the other hand, Rac, a sub-family of Rho, has been noticed to be associated with increased production of reactive oxygen species (ROS), which is responsible for vascular dysfunction in hypertension through the activation of NADPH oxidase. In the IVD, although residing in a hypoxic environment and getting energy mainly through glycolysis, NP cells still generated ROS through oxidative metabolism, especially in aged or degenerated discs with neovascularization. Chen et al. *Cell Physiol Biochem.* 2014; 34(4):1175-89 postulated that the increased apoptosis of NP cells under oxidative stress should be involved in the pathogenesis of IVD degeneration. To this aspect, inhibited Rac-1 activities could be the potential mechanism that contributes to the anabolic effect observed here with the NP cells treated by SV. Based on the present studies, it is important to understand how the SV metabolites affect the Rho family, including its sub-family Rac, in order to drive the consequences that are observed with the SV treatment.

Study Designs

CRISPR/Cas technology is used to efficiently disrupt small G-protein genes in ihNP cells. Single guide (sg) RNA is designed that has both high predicted activity and high specificity according to the webtools (benchling.com and CRISPRscan.org) to target Rho or Rac genes. To generate the sgRNA and Cas9 dual expression vectors, pairs of complementary DNA oligos with compatible overhangs are annealed and cloned into a modified pX458 vector that carries a U6 promoter to drive sgRNA expression and a ubiquitously expressed promoter to drive high-fidelity eSpCas9(1.1)-2A-GFP expression (modified from Addgene plasmids #43138 and #71814). sgRNA editing activity is evaluated in human 293T cells by the T7E1 assay (New England Biolabs), and compared side-by-side with EMX1 sgRNA that has been shown to modify the genome efficiently (Ran et al. Nat Protoc. 2013;8(11):2281-308, incorporated fully herein by reference). Validated sgRNA/Cas9 vectors are transfected into ihNP cells, and 48 hours later, transfected cells are sorted 1 cell per well into 96-well plates by GFP expression. Cell clones are cultured and genotyped to confirm bi-allelic non-sense mutations by Sanger sequencing. At least two independently targeted clones, as well as non-targeted wild-type clones, are used for the study.

Treatment Designs

Rho- or Rac1-deficient ihNP cells, along with wild-type control cells, are expanded, cultured and treated with each of the SV metabolites. Total RNA is extracted at Day 1, 2, 3, and 7 post-treatment for RT-qPCR to quantify gene expression levels of BMP-2.

Example 3

The following example illustrates meniscal repair and characterizes a torn meniscus repaired according to embodiments of the invention. Specifically this Example shows that treatment of an injured meniscus with injection of a hydrogel formulation of SVA stimulated chondrogenesis and resulted in verifiable meniscal repair, establishing SVA as a long-term viable therapeutic intervention for avascular meniscal tears that are currently considered irreparable.

Meniscal tears are a common knee injury with approximately one million corrective procedures performed annually in the United States. Menisci are essential components in the knee designed to transmit load across the tibiofemoral joint in order to decrease the amount of stressed placed on articular cartilage. Previously, the standard surgical treatment for an irreparable meniscal tear causing discomfort to the patient has been partial or total meniscectomy due to low healing potential and poor vascularity. However, research has shown that removal of the meniscus can lead to premature osteoarthritis due to increased stress placed on the articular cartilage. The purpose of this experiment/study is to characterize meniscal tissue repaired by site injection of a hydrogel composition comprising SVA.

Methods:

Female white New Zealand Rabbits (8-9 weeks); bilateral injuries were made to the avascular, anterior portion of the medial menisci using a 1.4 mm diameter k-wire. An SVA-hydrogel mixture was inserted into the defect to allow for sustained drug delivery at the injury site. The subject animals were allowed to heal for 8 weeks post injury. Hematoxylin & Eosin (H&E) and Safranin O (Safran-O) histological staining were utilized to analyze morphological changes in reparative tissue at the defect site. Collagen I, II and BMP-II immunohistochemistry were performed to determine the composition of the repaired tissue. Study groups included a control group with no injury, a control group with injury only, and a treatment group with injury+ SVA hydrogel repair treatment.

Results:

Previous studies conducted by the present inventor demonstrated that SVA can be utilized as a therapeutic agent to stimulate chondrogenesis and improve the degenerative changes associated with intervertebral disk disease in the rat model via upregulation of the bone morphogenic protein two (BMP-2) pathway. This pathway was also utilized in the present study, leading to the morphology seen in the meniscal repair tissue (FIG. 7B through FIG. 11B). While the repair tissue was still fragile at eight weeks post repair, these figures show that the tissue at the repair site contained organized, nucleated cells. In contrast to FIG. 7A that shows an absence of repaired tissue in the injury-only group at eight weeks post injury.

Proteoglycan content, collagen I, and collagen II are vital components to native meniscal tissue. The proteoglycans in the meniscus enable the tissue to maintain a high water content which is responsible for its ability to absorb compressive loads across the knee joint. Collagen I and II are responsible for the meniscus's capability to withstand tensile loads. The demonstration of proteoglycans, collagen I, and collagen II in the meniscal tissue repaired with the SVA hydrogel method (FIGS. 7B-11B) indicate similarities between the repaired meniscal tissue and native tissue.

Figure 8A:
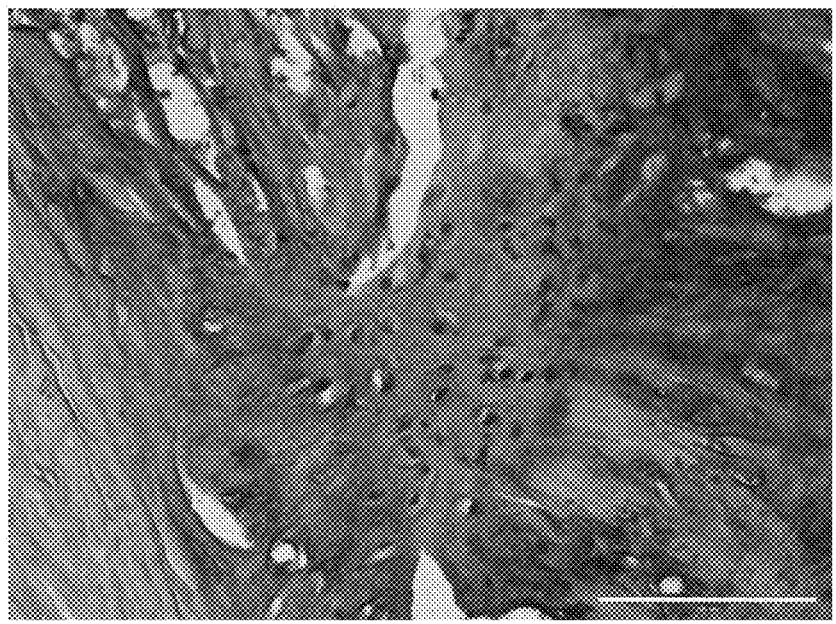
Figure 8B:
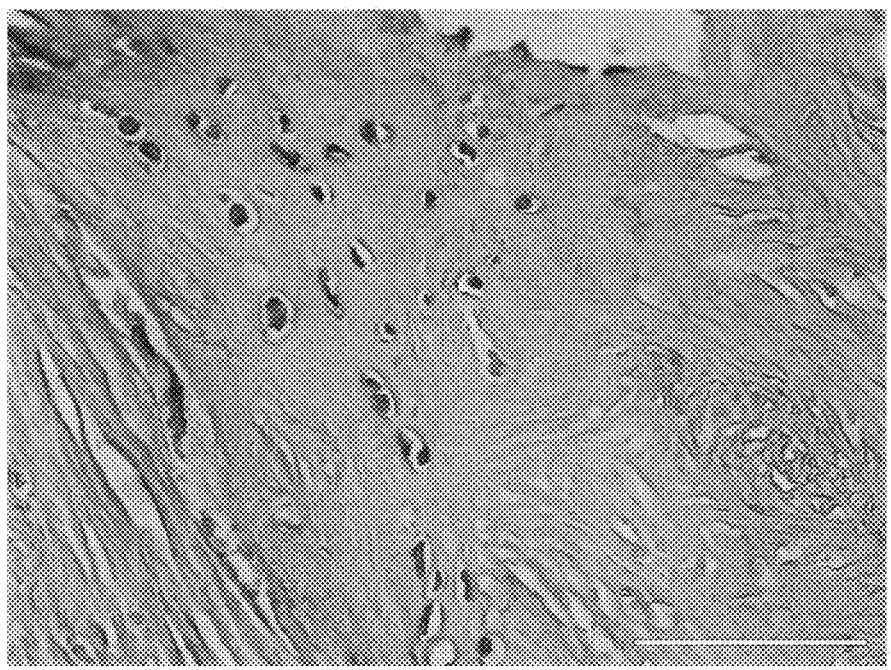
Figure 9A:
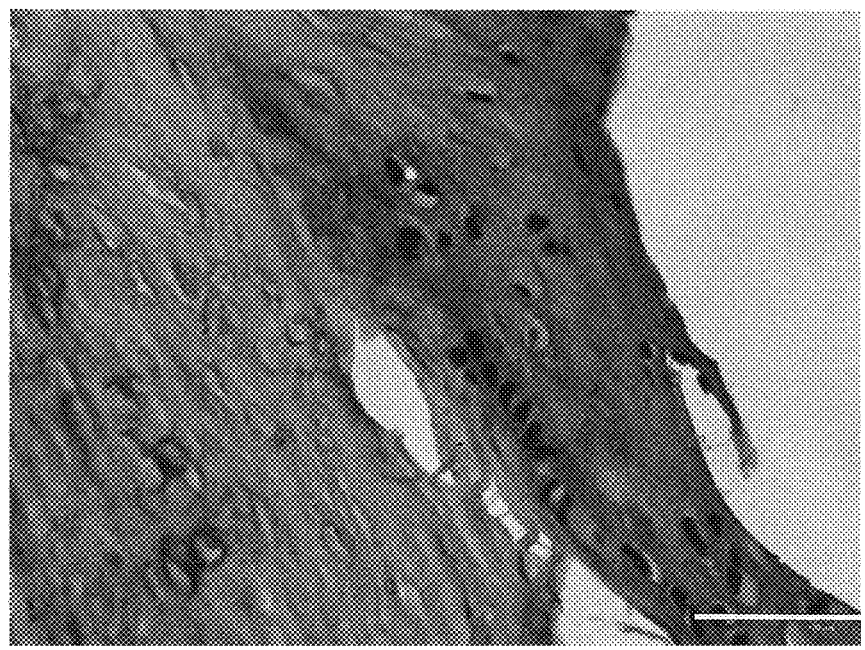
Figure 9B:
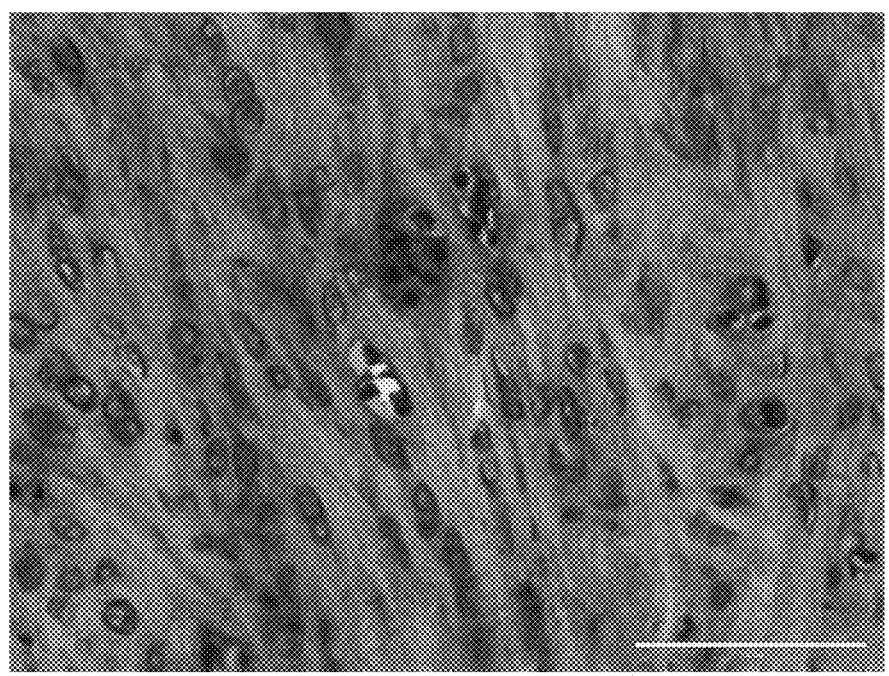
FIG. 9B same subject as 9A, 40X showing positive SAFO staining of organized cells located in the inner ⅓ of meniscal tissue.
Figure 10A:
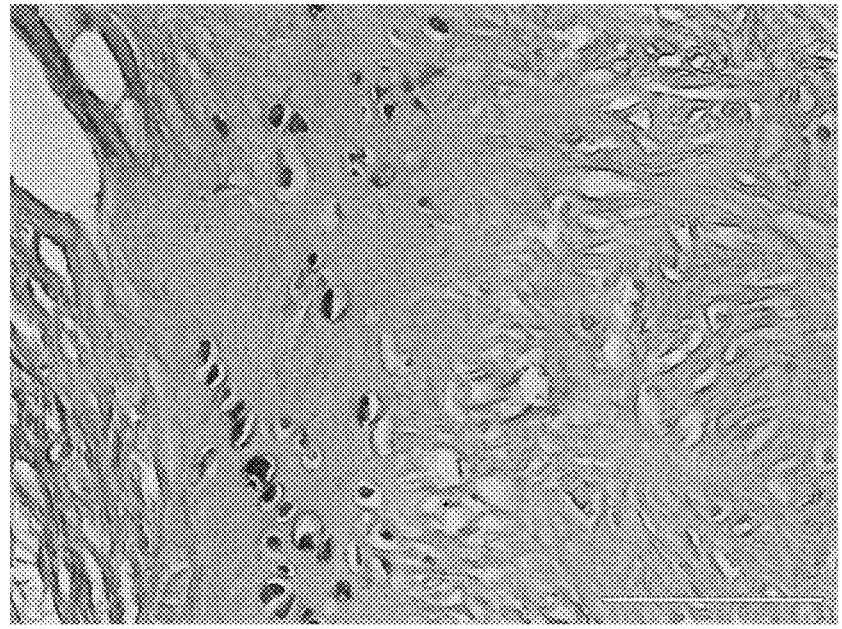
Figure 10B:
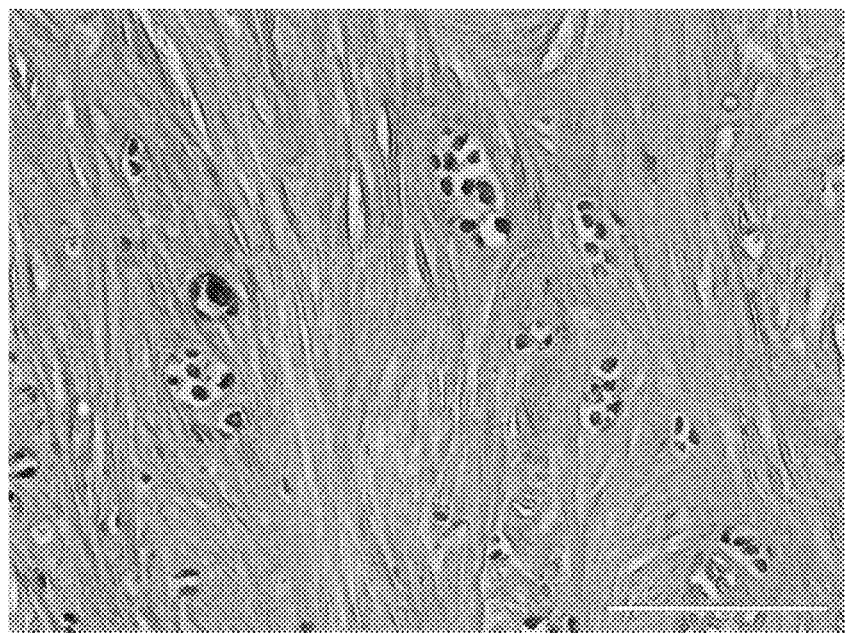
FIG. 10B same subject as FIG. 10A showing positive staining of organized cells for COL-I located in the inner ⅓ of meniscal tissue.
Figure 11A:
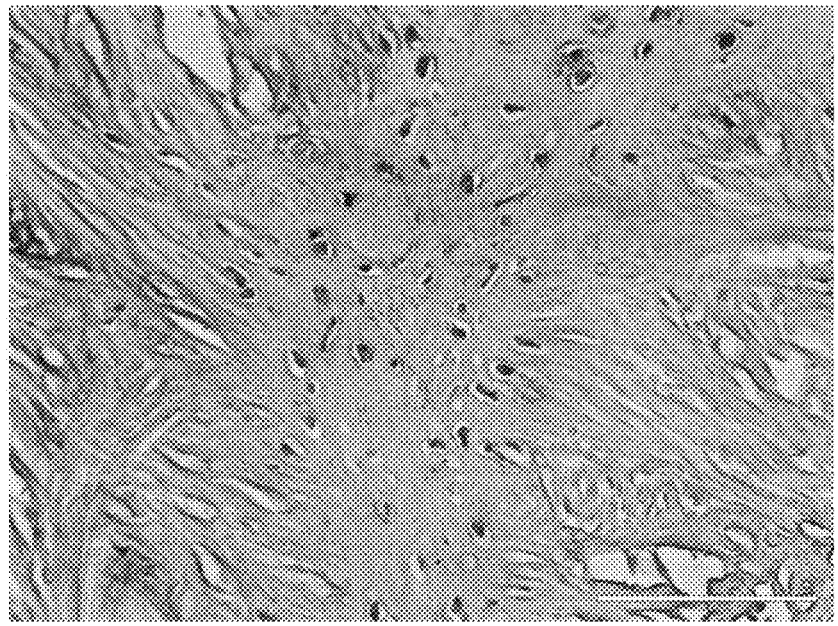
Figure 11B:
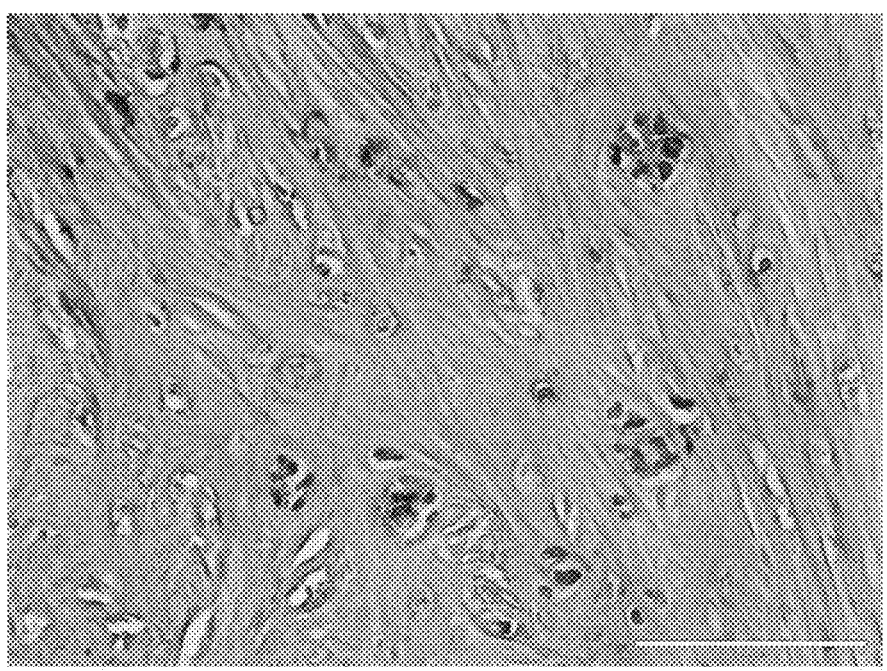
FIG. 11B same subject as FIG.

It was previously hypothesized that the SVA hydrogel would work via upregulation of the BMP-2 pathway. However, FIG. 8B shows that the tissue did not stain positive for BMP-2 at eight weeks post injury. A possible explanation for this finding is that the BMP-2 pathway is upregulated in the short period following repair to stimulate new tissue growth and is no longer active after eight weeks.

The entire disclosures of all publications cited herein are fully incorporated into the specification by reference.

The invention claimed is:

1. A method of repairing or retarding damage to injured avascular cartilaginous tissue in a subject in need thereof, the method comprising administering to the subject a composition comprising at least one oxidative metabolite of simvastatin (SV),
wherein the composition is administered directly to the avascular cartilaginous tissue by injection to a joint space, and
wherein the at least one oxidative metabolite of SV is selected from the group consisting of 3'-bydroxy simvastatin (hSV), 6'-exomethylene simvastatin (eSV), 3', 5'-dihydrodiol simvastatin (dSV), simvastatin-beta-hydroxy acid (SVA), and combinations thereof.

2. The method according to claim 1, wherein the composition is a controlled release formulation of the at least one oxidative metabolite of simvastatin (SV), and wherein said composition further comprises a hydrogel.

3. The method according to claim 1, wherein the at least one oxidative metabolite of SV comprises SVA.

4. The method according to claim 1, further comprising administering SV to the subject the SV and the oxidative metabolite of SV are administered simultaneously, in tandem, or within any time frame during which the subject is undergoing therapy for injured or degenerated cartilaginous tissue.

5. The method according to claim 1, wherein the avascular cartilaginous tissue is in a spinal disc.

6. The method according to claim 1, wherein the avascular cartilaginous tissue is in a joint.

7. The method according to claim 6, wherein the avascular cartilaginous tissue comprises meniscal cartilage.

8. The method according to claim 5, wherein the subject suffers from degenerative disc disease and the composition is administered by intradiscal administration.

9. The method according to claim 2, wherein the injection is carried out using a fluoroscope to guide a syringe carrying the controlled release formulation.

10. The method according to claim 2, wherein the hydrogel comprises a hydrophobic polymer and a hydrophilic polymer.

11. The method according to claim 10, wherein the polymers are homopolymers or copolymers.

12. The method according to claim 2, wherein the subject is a mammal.

13. The method according to claim 1, wherein the at least one oxidative metabolite of SV is selected from the group consisting of hSV, dSV, and combinations thereof.

14. The method according to claim 2, wherein an amount of the at least one oxidative metabolite of SV is dispersed within the hydrogel.

15. The method according to claim 2, wherein the hydrogel is selected from the group consisting of chitosan, cyclodextrin, p-dioxanone, ethylene glycol, ethylene glycol dimethacrylate, hyaluronic acid, hydroxyethyl methacrylate, methylene-bis-acrylamide, poly(acrylic acid), polyacrylamide, polycaprolactone, poly(ethylene glycol), poly(ethylene imine), poly(ethylene oxide), poly(ethyl methacrylate), poly(hydroxyethyl methacrylate), poly(hydroxypropyl methacrylamide), poly(lactic acid), poly(lactic-co-glycolic acid), poly(methyl methacrylate), poly(propylene oxide), poly(vinyl alcohol), poly(vinyl acetate), poly(vinyl amine), and combinations thereof.

16. The method according to claim 15, wherein the hydrogel comprises chitosan and/or hyaluronic acid.

17. The method according to claim 16, wherein the mass ratio of chitosan to hyaluronic acid is about 60:40.

* * * * *